(12) United States Patent
Kulprathipanja et al.

(10) Patent No.: US 7,991,504 B2
(45) Date of Patent: Aug. 2, 2011

(54) METHOD OF MEASURING EXTENT OF CURE OF BINDER IN PRODUCTS

(75) Inventors: Ames Kulprathipanja, Broomfield, CO (US); ChangQing Shen, Lakewood, CO (US); Richard Thomas Packard, Sedalia, CO (US); Kurt A. Lintelmann, Centennial, CO (US)

(73) Assignee: Johns Manville, Denver, CO (US)

( * ) Notice: Subject to any disclaimer, the term of this patent is extended or adjusted under 35 U.S.C. 154(b) by 625 days.

(21) Appl. No.: 12/217,581

(22) Filed: Jul. 7, 2008

(65) Prior Publication Data

US 2010/0001422 A1  Jan. 7, 2010

(51) Int. Cl.
B29C 39/00 (2006.01)
B29C 47/92 (2006.01)
G06F 19/00 (2011.01)
G01G 7/00 (2006.01)

(52) U.S. Cl. ........ 700/198; 700/109; 700/204; 700/208; 702/173; 264/40.4

(58) Field of Classification Search .......... 700/108–110, 700/198, 199, 204, 205, 208; 702/173; 264/40.4
See application file for complete search history.

(56) References Cited

U.S. PATENT DOCUMENTS 3,979,581 A * 9/1976 Reuland ................ 700/68
2005/0106091 A1 * 5/2005 Shapira et al. ............ 423/335
2005/0287675 A1 12/2005 Packard

* cited by examiner

*Primary Examiner* — Sean P Shechtman
(74) *Attorney, Agent, or Firm* — Robert D. Touslee

(57) ABSTRACT

A method for determining the extent of cure of binder in a product comprising heating a sample of the product to vaporize free moisture in the sample and expel vaporized free moisture from the sample, measuring cure moisture content of the product, measuring binder content of the product, calculating a product ratio of cure moisture content to binder content, and comparing the product ratio of cure moisture content to binder content to a predetermined desirable ratio of cure moisture content to binder content.

20 Claims, 4 Drawing Sheets

From Fig 1

METHOD OF MEASURING EXTENT OF CURE OF BINDER IN PRODUCTS

FIELD

The present disclosure generally relates to methods of measuring the cure of a binder in products. More specifically, the present disclosure relates to methods of quantitatively measuring the extent of cure or reactant cross-linking in binders, especially useful for finished insulation type products, and more specifically phenolic based binders.

BACKGROUND

Fiberglass insulation with binder that is insufficiently cured exhibits poor performance. Cure of phenolic resin is traditionally inspected through a change in color of the resin after (oven) curing. On non-dyed fiberglass products, the product changes from white to yellow after curing at the appropriate operating conditions. However, some binders are dyed black, which does not allow for visual inspection of the binder cure. Therefore, it would be desirable to provide a method of determining the degree of cure of products that include a phenolic binder.

SUMMARY

Provided is a method for determining the extent of cure of binder in a product comprising heating a sample of the product to vaporize free moisture in the sample and expel vaporized free moisture from the sample, measuring cure moisture content of the product, measuring binder content of the product, and calculating a product ratio of cure moisture content to binder content.

Measuring cure moisture content of the product comprises heating the sample in a weight-loss analyzer set to a cure moisture temperature set point, measuring weight change of the sample over time in the weight-loss analyzer while heating to the cure moisture temperature set point, and calculating cure moisture content of the sample using the weight change of the sample over time while heating to the cure moisture temperature set point. Heating to the cure moisture temperature set point vaporizes cure moisture in the sample and expels vaporized cure moisture from the sample.

Measuring binder content of the product comprises heating the sample in the weight-loss analyzer set to a binder temperature set point, measuring weight change of the sample over time in the weight-loss analyzer while heating to the binder temperature set point, and calculating binder content of the sample using the weight change of the sample over time while heating to the binder temperature set point. Heating to the binder temperature set point vaporizes binder in the sample and expels vaporized binder from the sample.

It has been found that by determining the extent of cure of binder in a product according to the present method, it is possible to get accurate and precise results that allow one to easily and appropriately adjust process parameters as desired or needed.

DETAILED DESCRIPTION

Provided is a method for determining the extent of cure of binder in a product. The product whose binder cure is to be measured include, for example, fiberglass insulation and non-woven glass mats. The binder can include, for example, phenolic, acrylic, latex or mixtures thereof. There are many known methods of producing products such as fiberglass insulation and glass mats. In general, fibers are formed into a network (e.g., a mat) and binder is applied to the network. Various methods are known for forming networks of fibers as well as applying binder to such networks. Typically, the products are then subjected to curing in order to heat the products and cure the binder to form the finished products. In an embodiment, the product whose binder cure is to be measured comprises a fiber glass insulation faced on one side with a non-woven mat. The (phenolic) binder can comprise black dye.

Phenolic Binder Cure Chemistry

Figure 1:
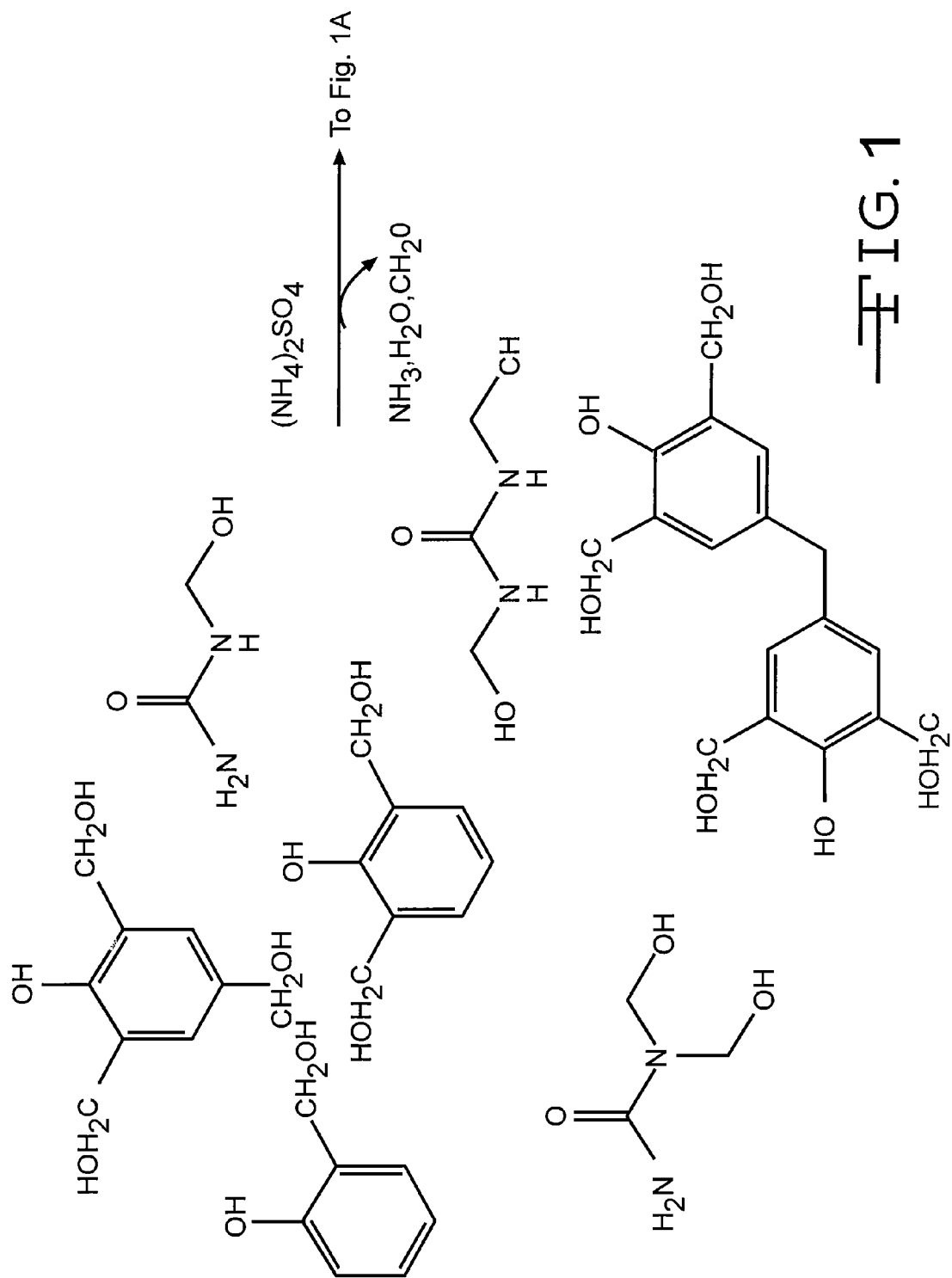
FIGS. 1 and 1A depict phenolic binder cure chemistry.
Figure 1A:
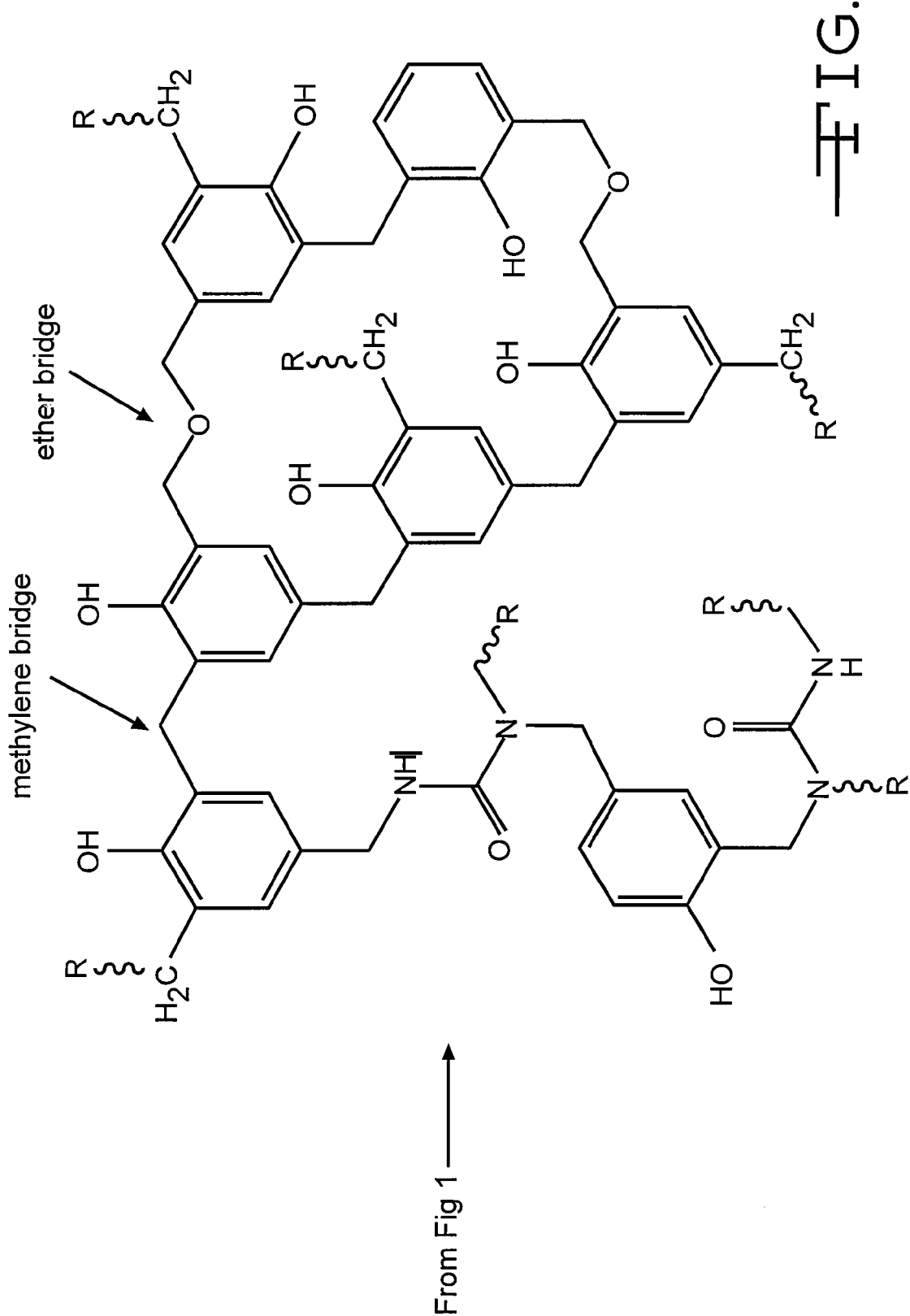

The degree of phenolic binder cure is a measure of the extent of reaction between the phenolic binder reactants. FIGS. 1 and 1A depict phenolic binder cure chemistry. During the phenolic binder cure process, water is produced as a by-product of the cross-linking reaction. The more the product is cured and the more binder reactants present in the product, the more water the binder will produce. Eventually, as the product is cured at extended periods of time and/or temperature, water production decreases as the reactants are consumed. When the product is completely cured (i.e., highest degree or extent of cure), no water will be produced as all the reactants are used up. Therefore, the amount of water generation during the cure process can indicate the extent of binder cure. The extent of cure reaction is increased by increasing temperature and length of cure time.

Because the amount of water by-product produced from the cure reaction also depends on the binder quantity of a particular sample, the extent of cure can be calculated by normalizing the water produced from the cross-linking reaction with the product binder content (i.e., dividing the amount of water produced from the cross-linking reaction by the product binder content). Thus, higher water/binder content ratio during manufacturing (cure) equals better cure, while lower water/binder content ratio after manufacturing cure equals better cure. Binder content remains unchanged for the same product. Theoretically, at complete cure, no water is produced after manufacturing cure so the water/binder content ratio equals zero.

Cure Correlation

A weight-loss analyzer or moisture analyzer, for example, the Computrac® MAX® 5000, manufactured by Arizona Instrument LLC, that can indirectly measure both water and binder content of a sample as losses in sample weight occur is used in the present method. In the first step of the present method, a sample of a product containing (phenolic) binder is heated to vaporize free moisture in the sample and expel vaporized free moisture from the sample. In particular, the sample is heated in the weight-loss analyzer set to a free moisture temperature set point. As used herein, the "free moisture temperature set point" is a temperature set point to which the weight-loss analyzer is set in order to withdraw free moisture from the product. As used herein, the "free moisture" of a product refers to the water content of the sample due to ambient conditions such as humidity, while the "cure moisture" of a product refers to the water by-product from the cure reaction described above.

In the second step of the present method, cure moisture content of the product is measured by heating the sample in the weight-loss analyzer set to a cure moisture temperature set point, measuring weight change, for example, rate weight change, of the sample over time in the weight-loss analyzer while heating to the cure moisture temperature set point, and calculating cure moisture content of the sample using the weight change of the sample over time while heating to the cure moisture temperature set point. Heating to the cure moisture temperature set point vaporizes cure moisture in the sample and expels vaporized cure moisture from the sample. As used herein, the "cure moisture temperature set point" is a temperature set point to which the weight-loss analyzer is set in order to withdraw cure moisture from the product.

In the third step of the present method, binder content of the product is measured by heating the sample in the weight-loss analyzer set to a binder temperature set point, measuring weight change of the sample over time in the weight-loss analyzer while heating to the binder temperature set point, and calculating binder content of the sample using the weight change of the sample over time while heating to the binder temperature set point. Heating to the binder temperature set point vaporizes binder in the sample and expels vaporized binder from the sample. As used herein, the "binder temperature set point" is a temperature set point to which the weight-loss analyzer is set in order to break down binder in the product and withdraw broken down binder from the product.

Finally, a product ratio of cure moisture content to binder content is calculated. As the weight-loss analyzer measures weight change of the sample over time while heating to the cure moisture temperature set point and binder temperature set point, a graph of weight change of the sample as a function of time can be plotted. From such a graph, as illustrated in FIG. 2, the product ratio of cure moisture content to binder content can be calculated by calculating an area under a curve of a plot of the rate weight change of the sample over time during measurement of the cure moisture content of the product (section B of FIG. 2) to provide a cure moisture content area, calculating an area under a curve of a plot of the rate weight change of the sample over time during measurement of the binder content of the product (section C of FIG. 2) to provide a binder content area, and dividing the cure moisture content area by the binder content area.

The calculated cure moisture content area and binder content area are not necessarily the actual values for cure moisture content and binder content for a specific product. A modification to the temperature set points or ramp rates will affect the values obtained for cure moisture content area and the binder content area, as time and temperature affect the binder curing chemistry. However, a correlation of calculated cure moisture content area to binder content area can be used to determine extent of cure, which eliminates the need for actual values.

The free moisture temperature set point is less than the cure moisture temperature set point, which is less than the binder temperature set point. For example, the free moisture temperature set point can be about 35° C. to about 110° C., the cure moisture temperature set point can be about 110° C. to about 350° C., and the binder temperature set point can be about 350° C. to about 800° C. The various set points will depend on the particular binder and potentially glass chemistry (i.e., a low-temperature curing binder chemistry would require lower set point temperatures than a high-temperature curing binder chemistry; furthermore, a low temperature melting glass chemistry could restrict the maximum binder burn-out temperature). In an embodiment, the free moisture temperature set point is about 65° C., the cure moisture temperature set point is about 190° C., and the binder temperature set point is about 600° C. With regard to the free moisture temperature set point, it is important that the temperature not be set too high so as to cause withdrawal of cure moisture from the product.

Figure 2:
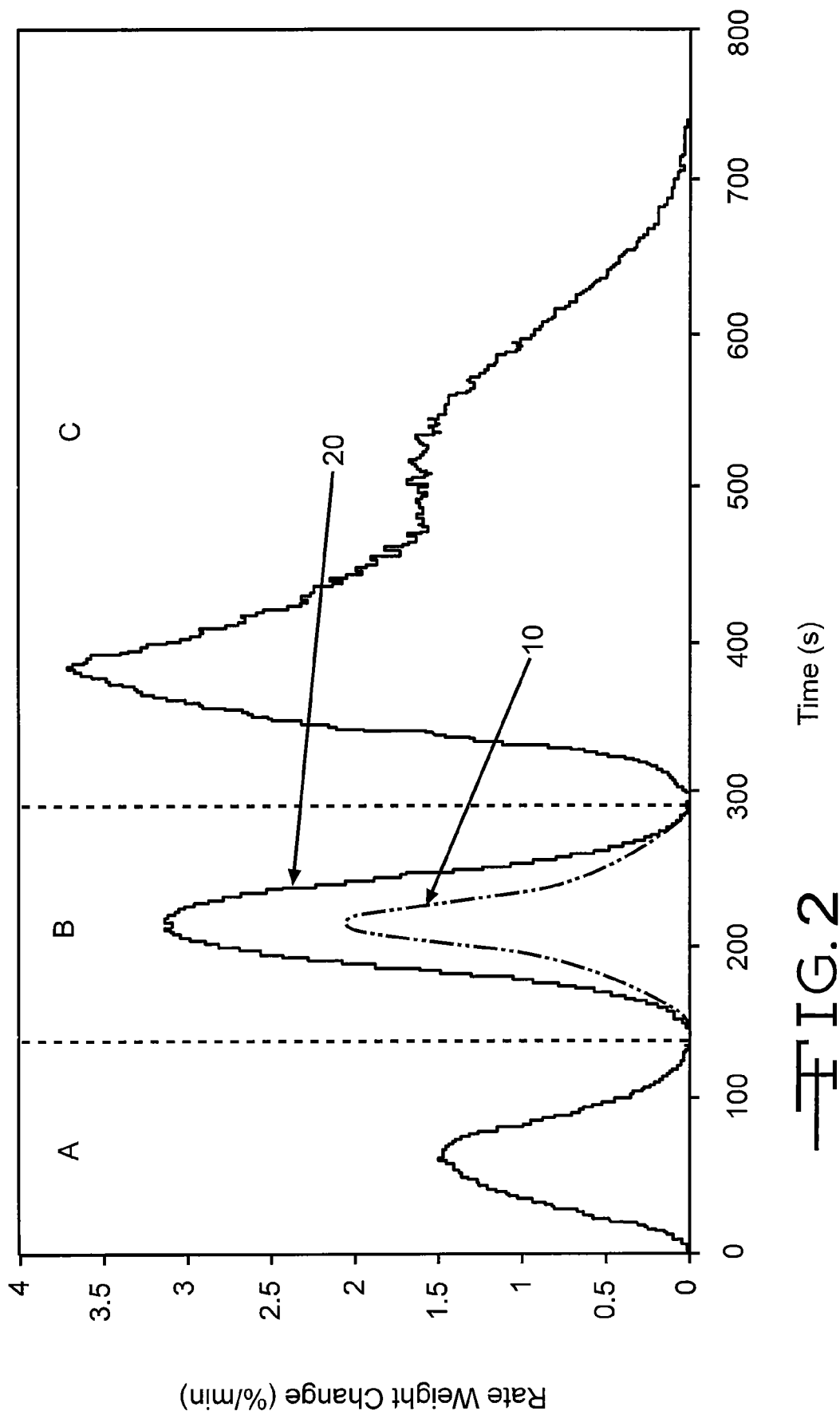
FIG. 2 is a graph of rate weight change of a product sample as a function of time while heating to three different temperature set points.

Weight change, for example, rate weight change, of the sample over time may also be measured in the weight-loss analyzer while heating to the free moisture temperature set point (section A and of FIG. 2). In an embodiment, the free moisture temperature set point is increased to the cure moisture temperature set point when a minimum rate weight change of the sample is achieved during measurement of the free moisture content of the product (as can be seen between section A and section B of FIG. 2) and the cure moisture temperature set point is increased to the binder temperature set point when a minimum rate weight change of the sample is achieved during measurement of the cure moisture content of the product (as can be seen between section B and section C of FIG. 2). Stated otherwise, the free moisture temperature set point is increased to the cure moisture temperature set point when no more free moisture in the sample is vaporized and expelled from the sample at the free moisture temperature set point and the cure moisture temperature set point is increased to the binder temperature set point when no more cure moisture in the sample is vaporized and expelled from the sample at the free moisture temperature set point.

Figure 3:
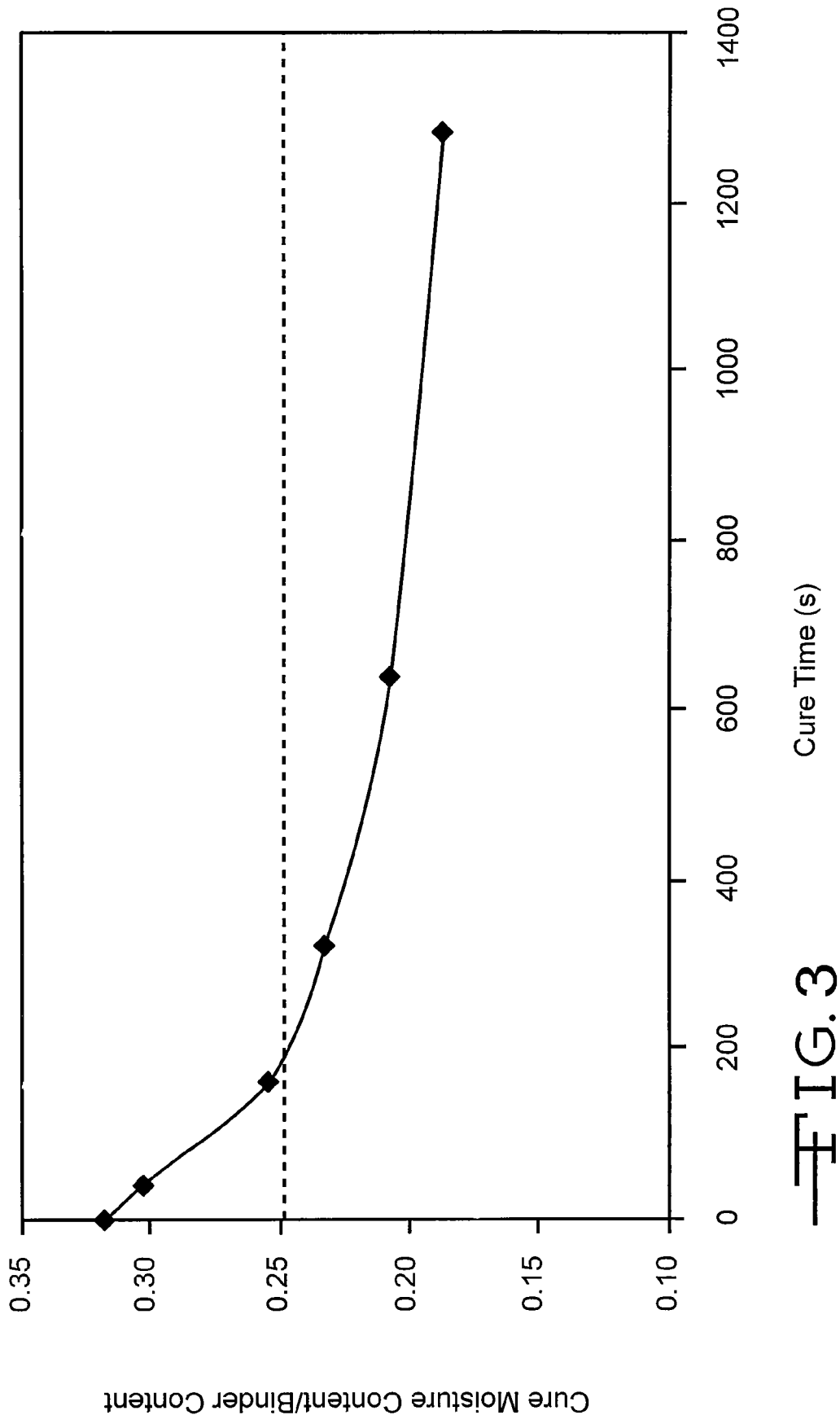
FIG. 3 is plot of extent of cure versus cure time for an originally uncured product.

By calculating the ratio of the cure moisture content to binder content, the extent of (phenolic) cure can be determined. Again referring to FIG. 2, a more cured product 10 will achieve a lower level of rate weight change compared to a less cured product (e.g., a partially cured product) 20 with the same binder content. FIG. 3 is a plot of extent of cure (i.e., cure moisture content/binder content) versus cure time for an originally uncured product. The uncured product was cured in an oven at 190° C. at different times to vary cure extent. As expected, degree of cure increased (i.e., less cure moisture generation) as cure time increased. The dashed line represents an exemplary minimum acceptable extent of cure (i.e., maximum cure moisture content/binder content).

In order to determine the extent of cure of (phenolic) binder in the product, the product ratio of cure moisture content to binder content is compared to a predetermined desirable ratio of cure moisture content to binder content to gauge the extent of cure of the binder. Such a predetermined desirable ratio may be tailored for a specific binder and/or a specific product. The predetermined desirable ratio is a range having an upper limit (i.e., low amount of cure) and a lower limit (i.e., high amount of cure). The predetermined desirable ratio of cure moisture content to binder content can be created to maximize and/or improve one or more product characteristics such as product density, product thickness, core delamination (i.e., how well the core stays together), facing adhesion (i.e., how well the core adheres to the facing), facing brittleness, and secondary facing adhesion (i.e., does applying a foil facing adhere to the product core).

A predetermined desirable ratio of cure moisture content to binder content is established by (previous) testing of samples (e.g., of the specific binder and/or product) known to have an acceptable or unacceptable amount of cure. In turn, whether a given sample has an acceptable or unacceptable amount of cure can be dependent on one or more sample characteristics such as, for example, core delamination, facing adhesion, facing brittleness, and secondary facing adhesion. In summary, determination of the extent of cure of (phenolic) binder in samples known to have an unacceptable amount of cure, coupled with determination of the extent of cure of (phenolic) binder in samples known to have an acceptable amount of cure, leads to an establishment of a (predetermined) desirable ratio of cure moisture content to binder content.

When the product ratio of cure moisture content to binder content is in a range of the predetermined desirable ratio of cure moisture content to binder content, the extent of cure of (phenolic) binder in the product is acceptable. However, the present method can further comprise modifying one or more process parameters during formation of the product if the product ratio of cure moisture content to binder content is not in a range of the predetermined desirable ratio of cure moisture content to binder content. Modifying one or more process parameters during formation of the product can comprise, for example, adjusting parameters of the product curing (e.g., curing time, curing temperature, moisture level during curing, air flow during curing, etc.). One or more product characteristics such as product density, product thickness, core delamination, facing adhesion, facing brittleness, and secondary facing adhesion can be improved by modifying the one or more process parameters during formation of the product.

While various embodiments have been described, it is to be understood that variations and modifications may be resorted to as will be apparent to those skilled in the art. Such variations and modifications are to be considered within the purview and scope of the claims appended hereto.

What is claimed is:

1. A method for determining the extent of cure of binder in a product, the method comprising:
   heating a sample of the product to vaporize free moisture in the sample and expel vaporized free moisture from the sample;
   measuring cure moisture content of the product, comprising:
      heating the sample in a weight-loss analyzer set to a cure moisture temperature set point, wherein heating to the cure moisture temperature set point vaporizes cure moisture in the sample and expels vaporized cure moisture from the sample;
      measuring weight change of the sample over time in the weight-loss analyzer while heating to the cure moisture temperature set point; and
      calculating cure moisture content of the sample using the weight change of the sample over time while heating to the cure moisture temperature set point;
   measuring binder content of the product, comprising:
      heating the sample in the weight-loss analyzer set to a binder temperature set point, wherein heating to the binder temperature set point vaporizes binder in the sample and expels vaporized binder from the sample;
      measuring weight change of the sample over time in the weight-loss analyzer while heating to the binder temperature set point; and
      calculating binder content of the sample using the weight change of the sample over time while heating to the binder temperature set point; and
   calculating a product ratio of cure moisture content to binder content.

2. The method of claim 1, wherein measuring weight change of the sample over time comprises measuring rate weight change of the sample over time.

3. The method of claim 1, wherein calculating the product ratio of cure moisture content to binder content comprises:
   calculating an area under a curve of a plot of the weight change of the sample over time during measurement of the cure moisture content of the product to provide a cure moisture content area;
   calculating an area under a curve of a plot of the weight change of the sample over time during measurement of the binder content of the product to provide a binder content area; and
   dividing the cure moisture content area by the binder content area.

4. The method of claim 1, wherein the binder comprises a binder selected from the group consisting of phenolic binder, acrylic binder, latex binder, and a mixture thereof.

5. The method of claim 1, wherein the binder comprises phenolic binder.

6. The method of claim 5, wherein the phenolic binder comprises black dye.

7. The method of claim 1, wherein the binder comprises black dye.

8. The method of claim 1, wherein the product comprises a fiber glass insulation faced on one side with a non-woven mat.

9. The method of claim 1, further comprising comparing the product ratio of cure moisture content to binder content to a predetermined desirable ratio of cure moisture content to binder content.

10. The method of claim 9, wherein the predetermined desirable ratio of cure moisture content to binder content is based on one or more product characteristics selected from the group consisting of product density, product thickness, core delamination, facing adhesion, facing brittleness, and secondary facing adhesion.

11. The method of claim 9, wherein when the product ratio of cure moisture content to binder content is in a range of the predetermined desirable ratio of cure moisture content to binder content, the extent of cure of binder in the product is acceptable.

12. The method of claim 9, further comprising modifying one or more process parameters during formation of the product if the product ratio of cure moisture content to binder content is not in a range of the predetermined desirable ratio of cure moisture content to binder content.

13. The method of claim 12, wherein modifying one or more process parameters during formation of the product comprises adjusting one or more of curing time, curing temperature, moisture level during curing, and air flow during curing.

14. The method of claim 12, wherein one or more product characteristics selected from the group consisting of product density, product thickness, core delamination, facing adhesion, facing brittleness, and secondary facing adhesion are improved by modifying the one or more process parameters during formation of the product.

15. The method of claim 1, wherein heating the sample to vaporize free moisture in the sample comprises heating the sample in a weight-loss analyzer set to a free moisture temperature set point.

16. The method of claim 15, wherein the free moisture temperature set point is less than the cure moisture temperature set point, which is less than the binder temperature set point.

17. The method of claim 15, wherein the free moisture temperature set point is about 35° C. to about 110° C., the cure moisture temperature set point is about 110° C. to about 350° C., and the binder temperature set point is about 350° C. to about 800° C.

18. The method of claim 15, wherein the free moisture temperature set point is about 65° C., the cure moisture temperature set point is about 190° C., and the binder temperature set point is about 600° C.

19. The method of claim 15, further comprising:

measuring weight change of the sample over time in the weight-loss analyzer while heating to the free moisture temperature set point, wherein:

the free moisture temperature set point is increased to the cure moisture temperature set point when a minimum rate weight change of the sample is achieved during measurement of the free moisture content of the product; and the cure moisture temperature set point is increased to the binder temperature set point when a minimum rate weight change of the sample is achieved during measurement of the cure moisture content of the product.

20. The method of claim 15, wherein:

the free moisture temperature set point is increased to the cure moisture temperature set point when no more free moisture in the sample is vaporized and expelled from the sample at the free moisture temperature set point; and the cure moisture temperature set point is increased to the binder temperature set point when no more cure moisture in the sample is vaporized and expelled from the sample at the free moisture temperature set point.

* * * * *